(12) United States Patent
Nara et al.

(10) Patent No.: US 7,964,744 B2
(45) Date of Patent: Jun. 21, 2011

(54) METHOD FOR PRODUCING A RUTHENIUM COMPLEX

(75) Inventors: Hideki Nara, Hiratsuka (JP); Noboru Sayo, Hiratsuka (JP); Takahiro Fujiwara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 58 days.

(21) Appl. No.: 12/540,794

(22) Filed: Aug. 13, 2009

(65) Prior Publication Data

US 2010/0076210 A1    Mar. 25, 2010

(30) Foreign Application Priority Data

Sep. 19, 2008 (JP) ................. 2008-241314

(51) Int. Cl.
*C07F 15/00* (2006.01)
(52) U.S. Cl. .......................................... 556/21
(58) Field of Classification Search ........... 556/21
See application file for complete search history.

(56) References Cited

U.S. PATENT DOCUMENTS 4,739,084 A   4/1988 Takaya et al.
5,488,172 A   1/1996 Cereghetti et al.

FOREIGN PATENT DOCUMENTS

| JP | 62-265293 A | 11/1987 |
| JP | 3-5492 A | 1/1991 |
| JP | 2003-528828 A | 9/2003 |
| WO | 01/64637 A1 | 9/2001 |
| WO | 2007/034975 A1 | 3/2007 |

OTHER PUBLICATIONS

Kitamura et al., Journal of Organic Chemistry, vol. 57, No. 14, pp. 4053-4054 (1992).*

Partial European Search Report ssued in EP 09 17 0582.2 mailed on Jan. 25, 2010.
Drießen-Hölscher, B., et al., "New Route to Biaryl Phosphanes with Axial Chirality as Ligands for Enantioselective Hydrogenations," Adv. Synth. Catal, 346, 979-982, 2004.
Masato Kitamura, et al., "Practical Synthesis of BINAP-Ruthenium (II) Dicarboxylate Complexes", J. Org. Chem., 1992, pp. 4053-4054, vol. 57.
Geldbach et al., "Chemistry of Ruthenium(II) Alkyl Binap Complexes: Novel Bonding, Cyclometalation, and P-C Bond Splitting," Organometallics, 2003, vol. 22, pp. 1443-1451.
Japanese Office Action issued in corresponding JP Application No. 2008-241314, dated Sep. 13, 2010.

* cited by examiner

*Primary Examiner* — Porfirio Nazario Gonzalez
(74) *Attorney, Agent, or Firm* — Sughrue Mion, PLLC

(57) ABSTRACT

Provided is a method for producing a ruthenium complex comprises the step of reacting a ruthenium compound represented by general formula (1):

$$[RuX(L)(PP)]X \quad (1),$$

wherein Ru represents a ruthenium atom; X represents a halogen atom; L represents an arene; and PP represents an optically active bisphosphine,
with a carboxylate salt represented by general formula (2):

$$R^1CO_2M \quad (2),$$

wherein M represents a monovalent cation; and $R^1$ represents a group selected from the group consisting of alkyl groups, haloalkyl groups, phenyl groups optionally having a substituent(s), 1-aminoalkyl groups and 1-amino-1-phenylalkyl groups,
to produce a ruthenium complex represented by general formula (3):

$$Ru(OCOR^1)_2(PP) \quad (3),$$

wherein $R^1$ represents the group selected from the group consisting of alkyl groups, haloalkyl groups, phenyl groups optionally having a substituent(s), 1-aminoalkyl groups and 1-amino-1-phenylalkyl groups; and PP represents the optically active bisphosphine.

4 Claims, No Drawings

METHOD FOR PRODUCING A RUTHENIUM COMPLEX

CROSS REFERENCE TO RELATED APPLICATION

This application claims priority based on Japanese Patent Application No. 2008-241314, filed Sep. 19, 2008, the contents of which is incorporated herein by reference in its entirety.

BACKGROUND OF THE INVENTION

1. Field of the Invention

The present invention relates to a method for producing a ruthenium complex including a carboxylate and an optically active bisphosphine as ligands (hereinafter, referred to as a carboxylate complex).

2. Brief Description of the Related Art

Carboxylate complexes are known to be a useful catalyst in asymmetric hydrogenation reactions. As the production methods thereof, the following methods are known, for example. In method (i), $Ru_2Cl_4(Lig)_2(NEt_3)$ produced from $[RuCl_2(cod)]_n$, a phosphine ligand (Lig) and triethylamine under reflux in toluene overnight is reacted with a carboxylate salt in an alcohol solvent such as methanol, ethanol and t-butanol, at 20° C. to 110° C, the solvent is evaporated to dryness; and the complex is extracted with an alcohol solvent (U.S. Pat. No. 4,739,084). In method (ii), $RuCl_2(binap)(dmf)_n$ synthesized by stirring $[RuCl_2(benzene)]_2$ and BINAP in a DMF solvent at 100° C. for 10 minutes is transferred to a separately-prepared solution of sodium acetate in methanol under an argon flow, the solution is stirred vigorously, degassed toluene and water are repeatedly added to wash the solution, the solution is concentrated to dryness, and the complex is recrystallized from toluene/hexane (J. Org. Chem., 57, 4053 (1992)). In method (iii), [Ru(p-cymene)(OAc)$_2$] obtained by reacting [RuCl$_2$(p-cymene)]$_2$ with a large excess of silver acetate in toluene is reacted with MeO-BIHEP in methylene chloride at 50° C. for 48 hours (U.S. Pat. No. 5,488,172).

However, in the conventional method (i), after the reflux in toluene overnight, the evaporation to dryness and solvent replacement have to be performed. Moreover, the resultant complex hardly has a uniform structure, and 40 equivalent of sodium acetate is used to convert the complex to a carboxylate complex. Furthermore, in order to produce a synthetic intermediate of the carboxylate complex, triethylamine, which is not needed in the end, needs to be added, and accordingly the method (i) is also disadvantageous in cost. In the method (ii), the condition in the DMF solvent at 100° C. for 10 minutes is unrealistic in industrial-scale production. Besides, since the reaction takes place at high temperature, the decomposition of the complex or the like is highly likely to occur. Moreover, as the procedure further proceeds, the solvents are added sequentially, and accordingly 100 equivalent volumes of the solvents are needed with respect to the target complex. The method (iii) has difficulties because [Ru(p-cymene)(OAc)$_2$] is a deliquescent and hard-to-handle intermediate, and the use of expensive silver acetate causes a cost problem, also. As described above, these conventional techniques have the following problem in common: the operations are complicated, and thus the production of by-products, the decomposition of the complexes and the like occur, in producing the carboxylate complexes. Accordingly, the reduction in yield, purity and the like is inevitable.

SUMMARY OF THE INVENTION

An object of the present invention is to provide a method that enables a carboxylate complex to be produced under a more moderate reaction condition and in an industrially simpler manner than those in conventional production methods.

As a result of the examination for achieving the above object, it has been discovered that a targeted carboxylate complex can be produced in fewer steps and in a simpler manner by reacting a carboxylate salt with a ruthenium compound represented by a general formula (1):

$$[RuX(L)(PP)]X \qquad (1),$$

wherein Ru represents a ruthenium atom, X represents a halogen atom, L represents an arene, and PP represents an optically active bisphosphine (hereinafter, may be referred to as a ruthenium compound (1)) which is used as a precursor of the complex product.

Specifically, the present invention provides a method for producing a ruthenium complex comprising the step of reacting a ruthenium compound represented by general formula (1):

$$[RuX(L)(PP)]X \qquad (1),$$

wherein Ru represents a ruthenium atom, X represents a halogen atom, L represents an arene, and PP represents an optically active bisphosphine,
with a carboxylate salt represented by general formula (2):

$$R^1CO_2M \qquad (2),$$

wherein M represents a monovalent cation, and $R^1$ represents a group selected from the group consisting of alkyl groups, haloalkyl groups, phenyl groups optionally having a substituent(s), 1-aminoalkyl groups and 1-amino-1-phenylalkyl groups,
to produce a ruthenium complex represented by general formula (3):

$$Ru(OCOR^1)_2(PP) \qquad (3),$$

wherein, $R^1$ represents a group selected from the group consisting of alkyl groups, haloalkyl groups, phenyl groups optionally having a substituent(s), 1-aminoalkyl groups and 1-amino-1-phenylalkyl groups, and PP represents an optically active bisphosphine.

Moreover, the present invention provides a method for producing a ruthenium complex comprising the step of reacting a ruthenium compound represented by general formula (7):

$$[RuX_2(L)]_n \qquad (7),$$

wherein Ru represents a ruthenium atom, X represents a halogen atom, L represents an arene, and n represents a natural number of 2 or higher,
with an optically active bisphosphine and a carboxylate salt represented by general formula (2):

$$R^1CO_2M \qquad (2),$$

wherein M represents a monovalent cation, and $R^1$ represents a group selected from the group consisting of alkyl groups, haloalkyl groups, phenyl groups optionally having a substituent(s), 1-aminoalkyl groups and 1-amino-1-phenylalkyl groups,
to produce a ruthenium complex represented by general formula (3):

$$Ru(OCOR^1)_2(PP) \qquad (3),$$

wherein $R^1$ represents the group selected from the group consisting of alkyl groups, haloalkyl groups, phenyl groups optionally having a substituent(s), 1-aminoalkyl groups and 1-amino-1-phenylalkyl groups, and PP represents the optically active bisphosphine.

The present invention enables a carboxylate complex to be produced under a moderate condition and by an industrially simple operation.

DESCRIPTION OF THE PREFERRED EMBODIMENTS

Hereinbelow, the present invention will be described in detail.

A method for producing a ruthenium complex production method represented by a general formula (3):

$$Ru(OCOR^1)_2(PP) \qquad (3)$$

of the present invention is characterized by reacting a ruthenium compound represented by a general formula (1):

$$[RuX(L)(PP)]X \qquad (1)$$

with a carboxylate salt represented by a general formula (2):

$$R^1CO_2M \qquad (2)$$

(hereinafter, it may be referred to as a carboxylate salt (2)).

In the formula (1), X represents a halogen atom. Examples of the halogen atom include a chlorine atom, a bromine atom and an iodine atom.

In the formula (1), L represents an arene, preferably benzene optionally having an alkyl substituent, and more preferably p-cymene, benzene, mesitylene, toluene, or o-, m- or p-xylene.

In the formula (1), PP represents an optically active bisphosphine. An example thereof is an optically active bisphosphine represented by the following general formula (6):

$$R^2R^3P-Q-PR^4R^5 \qquad (6),$$

wherein $R^2$, $R^3$, $R^4$ and $R^5$ each independently represent an aryl group optionally having a substituent, a cycloalkyl group optionally having a substituent, or an alkyl group optionally having a substituent. Each pair of $R^2$ and $R^3$ and/or $R^4$ and $R^5$ may form a ring. Q represents a divalent arylene group optionally having a substituent or represents a ferrocenediyl group optionally having a substituent).

In the formula, an example of the aryl group optionally having a substituent, which is represented by $R^2$, $R^3$, $R^4$ and $R^5$, is an aryl group having 6 to 14 carbon atoms. Specific examples thereof include a phenyl group, a naphthyl group, an anthryl group, a phenanthryl group and a biphenyl group. These aryl groups optionally have one or more substituents. Examples of the substituent include an alkyl group, an alkoxy group, an aryl group and a heterocyclic group.

An example of the alkyl group as the substituent in the aryl group is a linear or branched alkyl group having, for example, 1 to 15 carbon atoms, preferably 1 to 10 carbon atoms, and more preferably 1 to 6 carbon atoms. Specific examples thereof include a methyl group, an ethyl group, a n-propyl group, an isopropyl group, a n-butyl group, a s-butyl group, an isobutyl group and a t-butyl group.

An example of the alkoxy group as the substituent in the aryl group is a linear or branched alkoxy group having, for example, 1 to 6 carbon atoms. Specific examples thereof include a methoxy group, an ethoxy group, a n-propoxy group, an isopropoxy group, a n-butoxy group, a s-butoxy group, an isobutoxy group and a t-butoxy group.

An example of the aryl group as the substituent in the aryl group is an aryl group having, for example, 6 to 14 carbon atoms. Specific examples thereof include a phenyl group, a naphthyl group, an anthryl group, a phenanthryl group and a biphenyl group.

Examples of the heterocyclic group as the substituent in the aryl group include an aliphatic heterocyclic group and an aromatic heterocyclic group. An example of the aliphatic heterocyclic group is a 5- to 8-membered (preferably, 5- or 6-membered) monocyclic, polycyclic or condensed aliphatic heterocyclic group having 2 to 14 carbon atoms and at least one heteroatom (preferably, 1 to 3 heteroatoms) such as a nitrogen atom, an oxygen atom and a sulfur atom. Specific examples of the aliphatic heterocyclic group include a 2-oxopyrrolidyl group, a piperidino group, a piperazinyl group, a morpholino group, a tetrahydrofuryl group, a tetrahydropyranyl group and a tetrahydrothienyl group. Meanwhile, an example of the aromatic heterocyclic group is a 5- to 8-membered (preferably, 5- or 6-membered) monocyclic, polycyclic or condensed aromatic heterocyclic group having 2 to 15 carbon atoms and at least one heteroatom (preferably, 1 to 3 heteroatoms) such as a nitrogen atom, an oxygen atom and a sulfur atom. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzoimidazolyl group, a benzoxazolyl group and a benzothiazolyl group.

Moreover, an example of the cycloalkyl group optionally having a substituent, which is represented by $R^2$, $R^3$, $R^4$ and $R^5$, is a 5-membered or 6-membered cycloalkyl group. Preferable examples of the cycloalkyl group include a cyclopentyl group and a cyclohexyl group. One or more positions of the ring of each of these cycloalkyl groups may be replaced with substituents such as an alkyl group and an alkoxy group that are listed above as the substituent in the aryl group.

Furthermore, an example of the alkyl group optionally having a substituent, which is represented by $R^2$, $R^3$, $R^4$ and $R^5$, is a linear or branched alkyl group having, for example, 1 to 15 carbon atoms, preferably 1 to 10 carbon atoms, and more preferably 1 to 6 carbon atoms. Specific examples thereof include a methyl group, an ethyl group, a n-propyl group, an isopropyl group, a n-butyl group, a s-butyl group, an isobutyl group, a t-butyl group, a pentyl group and a hexyl group. These alkyl groups may have one or more substituents. Examples of such a substituent include an alkoxy group and a halogen atom.

In addition, examples of the ring optionally formed by each pair of $R^2$ and $R^3$ and/or $R^4$ and $R^5$ include a 4-membered ring, a 5-membered ring and a 6-membered ring, each ring containing a phosphorus atom bonded to the corresponding pair of $R^2$ and $R^3$ or $R^4$ and $R^5$. Specific examples of such rings include a phosphetane ring, a phospholane ring, a phosphinane ring, a 2,4-dimethylphosphetane ring, a 2,4-diethylphosphetane ring, a 2,5-dimethylpholane ring, a 2,5-diethylphospholane ring, a 2,6-dimethylphosphinane ring and a 2,6-diethylphosphinane ring. These rings may be optically active.

Examples of the divalent arylene group optionally having a substituent, which is represented by Q, include a phenylene group, a biphenyldiyl group and a binaphthalenediyl group. Examples of the phenylene group include o- and m-phenylene groups. The phenylene group may have a substituent as follows: an alkyl group such as a methyl group, an ethyl group, a n-propyl group, an isopropyl group, a n-butyl group, a s-butyl group, an isobutyl group and a t-butyl group; an alkoxy group such as a methoxy group, an ethoxy group, a n-propoxy group, an isopropoxy group, a n-butoxy group, a s-butoxy group, an isobutoxy group and a t-butoxy group; a hydroxy group; an amino group; a substituted amino group; and the like. The biphenyldiyl group and the binaphthalenediyl group preferably have a 1,1'-biaryl-2,2'-diyl structure. The biphenyldiyl group and the binaphthalenediyl group may have a substituent as follows: an alkyl group as described above; an alkoxy group as described above; an alkylenedioxy group such as a methylenedioxy group, an ethylenedioxy group and a trimethylenedioxy group; a hydroxy group; an amino group; a substituted amino group; and the like. Meanwhile, the ferrocenediyl group may also have a substituent. Examples of the substituent include those described above, an alkyl group as described above, an alkoxy group as described above, an alkylenedioxy group as described above, a hydroxy group, an amino group, a substituted amino group, and the like.

Specific examples of the optically active bisphosphine represented by the general formula (6) may be publicly-known bisphosphines. Among them, one example is a compound represented by the following general formula (4):

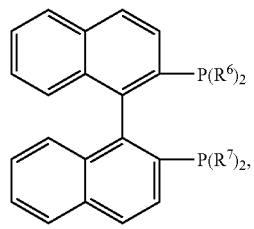

(4)

wherein $R^6$ and $R^7$ each independently represent: a phenyl group optionally having a substituent selected from the group consisting of halogen atoms, alkyl groups and alkoxy groups; a cyclopentyl group; or a cyclohexyl group)

An example of the alkyl group as the substituent in the phenyl group, which is represented by $R^6$ and $R^7$ above, is a linear or branched alkyl group having 1 to 6 carbon atoms, such as a methyl group and a t-butyl group. An example of the alkoxy group as the substituent in the phenyl group is a linear or branched alkoxy group having 1 to 6 carbon atoms, such as a methoxy group and a t-butoxy group. Examples of the halogen atom as the substituent in the phenyl group include a chlorine atom, a bromine atom and a fluorine atom. A multiple number of these substituents may be introduced into the phenyl group.

Specific examples of $R^6$ and $R^7$ include a phenyl group, a p-tolyl group, a m-tolyl group, an o-tolyl group, a 3,5-xylyl group, a 3,5-di-t-butylphenyl group, a p-t-butylphenyl group, a p-methoxyphenyl group, a 3,5-di-t-butyl-4-methoxyphenyl group, a p-chlorophenyl group, a m-chlorophenyl group, a p-fluorophenyl group, a m-fluorophenyl group, a cyclopentyl group and a cyclohexyl group.

The binaphthyl ring which is a basic structure of the compound represented by the general formula (4) may have a substituent, and examples thereof include: an alkyl group such as a methyl group and a t-butyl group; an alkoxy group such as a methoxy group and a t-butoxy group; a trialkylsilyl group such as a trimethylsilyl group, a triisopropylsilyl group and a t-butyldimethylsilyl group; and a triarylsilyl group such as a triphenylsilyl group.

Another specific example of the optically active bisphosphine represented by the general formula (6) is a compound represented by the following general formula (5):

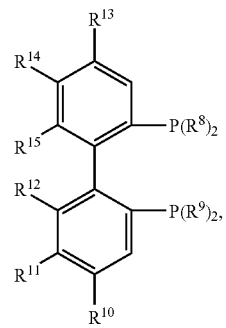

(5)

wherein $R^8$ and $R^9$ each independently represent: a phenyl group optionally having a substituent selected from the group consisting of halogen atoms, alkyl groups and alkoxy groups; a cyclopentyl group; or a cyclohexyl group; $R^{10}$, $R^{11}$, $R^{13}$ and $R^{14}$ each independently represent an atom or a group selected from the group consisting of a hydrogen atom, alkyl groups, alkoxy groups, acyloxy groups, halogen atoms, haloalkyl groups and dialkylamino groups; $R^{12}$ and $R^{15}$ each independently represent a group selected from the group consisting of alkyl groups, alkoxy groups, acyloxy groups, halogen atoms, haloalkyl groups and dialkylamino groups; any two groups of $R^{10}$, $R^{11}$ and $R^{12}$ may together form a methylene chain optionally having a substituent, or a (poly)methylenedioxy group optionally having a substituent; any two groups of $R^{13}$, $R^{14}$ and $R^{15}$ may together form a methylene chain optionally having a substituent, or a (poly)methylenedioxy group optionally having a substituent; and $R^{12}$ and $R^{15}$ may together form a methylene chain optionally having a substituent, or a (poly)methylenedioxy group optionally having a substituent.

An example of the alkyl group as the substituent in the phenyl group represented by $R^8$ and $R^9$ above, is a linear or branched alkyl group having 1 to 6 carbon atoms, such as a methyl group and a t-butyl group. An example of the alkoxy group as the substituent in the phenyl group is a linear or branched alkoxy group having 1 to 6 carbon atoms, such as a methoxy group and a t-butoxy group. Examples of the halogen atom as the substituent in the phenyl group include a chlorine atom, a bromine atom and a fluorine atom. A multiple number of these substituents may be introduced into the phenyl group. Specific examples of $R^8$ and $R^9$ include a phenyl group, a p-tolyl group, a m-tolyl group, an o-tolyl group, a 3,5-xylyl group, a 3,5-di-t-butylphenyl group, a p-t-butylphenyl group, a p-methoxyphenyl group, a 3,5-di-t-butyl-4-methoxyphenyl group, a p-chlorophenyl group, a m-chlorophenyl group, a p-fluorophenyl group, a m-fluorophenyl group, a cyclopentyl group and a cyclohexyl group.

Moreover, an example of the alkyl group represented by $R^{10}$ to $R^{15}$ is a linear or branched alkyl group having 1 to 6 carbon atoms, such as a methyl group and a t-butyl group. An example of the alkoxy group represented by $R^{10}$ to $R^{15}$ is a linear or branched alkoxy group having 1 to 6 carbon atoms, such as a methoxy group and a t-butoxy group. An example of the acyloxy group represented by $R^{10}$ to $R^{15}$ is an acyloxy group having 2 to 10 carbon atoms, such as an acetoxy group, a propanoyloxy group, a trifluoroacetoxy group and a benzoyloxy group. Examples of the halogen atom represented by $R^{10}$ to $R^{15}$ include a chlorine atom, a bromine atom and a fluorine atom. An example of the haloalkyl group represented by $R^{10}$ to $R^{15}$ is a haloalkyl group having 1 to 4 carbon atoms, such as a trifluoromethyl group. Examples of the dialkylamino group represented by $R^{10}$ to $R^{15}$ include a dimethylamino group and a diethylamino group.

When any two groups of $R^{10}$, $R^{11}$ and $R^{12}$ form the methylene chain optionally having a substituent, or when any two groups of $R^{13}$, $R^{14}$ and $R^{15}$ form the methylene chain optionally having a substituent, the methylene chain preferably has, for example, 3 to 5 carbon atoms. Specific examples of the methylene chain include a trimethylene group, a tetramethylene group and a pentamethylene group. Examples of the substituent in the methylene chain include an alkyl group and a halogen atom. Specific examples thereof include an alkyl group having 1 to 6 carbon atoms as described above and a fluorine atom.

Furthermore, when any two groups of $R^{10}$, $R^{11}$ and $R^{12}$ form the (poly)methylenedioxy group optionally having a substituent, or when any two groups of $R^{13}$, $R^{14}$ and $R^{15}$ form the (poly)methylenedioxy group optionally having a substituent, specific examples of the (poly)methylenedioxy group include a methylenedioxy group, an ethylenedioxy group and a trimethylenedioxy group. Examples of the substituent that the (poly)methylenedioxy group has include an alkyl group and a halogen atom. Specific examples thereof include an alkyl group having 1 to 6 carbon atoms as described above and a fluorine atom.

Specific examples of the optically active bisphosphine compounds represented by the general formulas (4) and (5) include 2,2'-bis(diphenylphosphino)-1,1'-binaphthyl (BINAP), 2,2'-bis[di(p-tolyl)phosphino]-1,1'-binaphthyl (Tol-BINAP), 2,2'-bis[di(m-tolyl)phosphino]-1,1'-binaphthyl, 2,2'-bis[di(3,5-xylyl)phosphino]-1,1'-binaphthyl (DM-BINAP), 2,2'-bis[di(p-t-butylphenyl)phosphino]-1,1'-binaphthyl, 2,2'-bis[di(p-methoxyphenyl)phosphino]-1,1'-binaphthyl, 2,2'-bis[di(3,5-di-t-butyl-4-methoxyphenyl) phosphino]-1,1'-binaphthyl, 2,2'-bis[di(cyclopentyl) phosphino]-1,1'-binaphthyl, 2,2'-bis[di(cyclohexyl) phosphino]-1,1'-binaphthyl, 2,2'-bis(diphenylphosphino)-5,5',6,6',7,7',8,8'-octahydro-1,1'-binaphthyl ($H_8$-BINAP), 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di-3,5-xylylphosphino)-5,5',6,6',7,7',8,8'-octahydro-1,1'-binaphthyl, 2,2'-bis(di-p-t-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis (dicyclohexylphosphino)-5,5',6,6',7,7',8,8'-octahydro-1,1'-binaphthyl, ((4,4'-bi-1,3-benzodioxol)-5,5'-diyl)bis (diphenylphosphine) (SEGPHOS), (4,4'-bi-1,3-benzodioxol)-5,5'-diyl)bis(di(3,5-dimethylphenyl) phosphine) (DM-SEGPHOS), ((4,4'-bi-1,3-benzodioxol)-5,5'-diyl)bis(di(3,5-di-t-butyl-4-methoxyphenyl)phosphine) (DTBM-SEGPHOS), ((4,4'-bi-1,3-benzodioxol)-5,5'-diyl) bis(di(4-methoxyphenyl)phosphine), ((4,4'-bi-1,3-benzodioxol)-5,5'-diyl)bis(dicyclohexylphosphine), ((4,4'-bi-1,3-benzodioxol)-5,5'-diyl)bis(bis(3,5-di-t-butylphenyl) phosphine), 2,2'-bis(diphenylphosphino)-4,4',6,6'-tetramethyl-5,5'-dimethoxy-1,1'-biphenyl, 2,2'-bis(di-p-methoxyphenylphosphino)-4,4',6,6'-tetramethyl-5,5'-dimethoxy-1,1'-biphenyl, 2,2'-bis(diphenylphosphino)-4,4',6,6'-tetra(trifluoromethyl)-5,5'-dimethyl-1,1'-biphenyl, 2,2'-bis(diphenylphosphino)-4,6-di(trifluoromethyl)-4',6'-dimethyl-5'-methoxy-1,1'-biphenyl, 2-dicyclohexylphosphino-2'-diphenylphosphino-4,4',6,6'-tetramethyl-5,5'-dimethoxy-1,1'-biphenyl, 2,2'-bis(diphenylphosphino)-6,6'-dimethyl-1,1'-biphenyl, 2,2'-bis(diphenylphosphino)-4,4',6,6'-tetramethyl-1,1'-biphenyl, 2,2'-bis (diphenylphosphino)-3,3',6,6'-tetramethyl-1,1'-biphenyl), 2,2'-bis(diphenylphosphino)-4,4'-difluoro-6,6'-dimethyl-1,1'-biphenyl, 2,2'-bis(diphenylphosphino)-4,4'-bis(dimethylamino)-6,6'-dimethyl-1,1'-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 1,11-bis(diphenylphosphino)-5,7-dihydrobenzo[c,e]oxepin, 2,2'-bis(diphenylphosphino)-6,6'-dimethoxy-1,1'-biphenyl, 2,2'-bis(diphenylphosphino)-5,5',6,6'-tetramethoxy-1,1'-biphenyl, 2,2'-bis(di-p-tolylphosphino)-6,6'-dimethoxy-1,1'-biphenyl, 2,2'-bis(diphenylphosphino)-4,4',5,5',6,6'-hexamethoxy-1,1'-biphenyl, 1,2-bis(2,5-dimethylphospholano)benzene, 1,2-bis(2,5-diethylphospholano)benzene, 1,2-bis(2,5-diisopropylphospholano)benzene, 1-(2,5-dimethylphospholano)-2-(diphenylphosphino)benzene and 1,1'-bis(2,4-diethylphosphotano)ferrocene.

Besides, specific example of the optically active bisphosphine compound that can be used in the present invention include N,N-dimethyl-1-[1',2-bis(diphenylphosphino)ferrocenyl]ethylamine, 2,3-bis(diphenylphosphino)butane, 1-cyclohexyl-1,2-bis(diphenylphosphino)ethane, 2,3-o-isopropylidene-2,3-dihydroxy-1,4-bis(diphenylphosphino)butane, 1,2-bis[(o-methoxyphenyl)phenylphosphino]ethane, 1,2-bis (2,5-dimethylphospholano)ethane, N,N'-bis(diphenylphosphino)-N,N'-bis(1-phenylethyl)ethylenediamine, 1,2-bis (diphenylphosphino)propane, 2,4-bis(diphenylphosphino) pentane, cyclohexylanisylmethylphosphine (CAMP), 2,3-bis (diphenylphosphino)-5-norbornene (NORPHOS), 3,4-bis (diphenylphosphino)-1-benzylpyrrolidine (DEGPHOS), 1-[1',2-bis(diphenylphosphino)ferrocenyl]ethyl alcohol (BPPFOH) and 2,2'-bis(diphenylphosphino)-1,1'-dicyclopentane (BICP).

The ruthenium compound (1) used in the production method of the present invention is preferably [RuX(arene) (PP)]X. In the formula, X is selected from the group consisting of Cl, Br and I, the arene is selected from the group consisting of p-cymene, benzene, mesitylene, toluene, o-xylene, m-xylene and p-xylene, and PP is selected from the group consisting of BINAP, TOL-BINAP, $H_8$-BINAP, DM-BINAP, SEGPHOS, DM-SEGPHOS and DTBM-SEGPHOS. More preferably, the ruthenium compound (1) is [RuCl(p-cymene)(PP)]Cl, [RuBr(p-cymene)(PP)]Br, [RuI (p-cymene)(PP)]I, [RuCl(benzene)(PP)]Cl, [RuBr(benzene) (PP)]Br, [RuI(benzene)(PP)]I, [RuCl(mesitylene)(PP)]Cl, [RuBr(mesitylene)(PP)]Br, [RuI(mesitylene)(PP)]I, [RuCl (toluene)(PP)]Cl, [RuBr(toluene)(PP)]Br, [RuI(toluene) (PP)]I, [RuCl(o-xylene)(PP)]Cl, [RuBr(o-xylene)(PP)]Br, [RuI(o-xylene)(PP)]I, [RuCl(m-xylene)(PP)]Cl, [RuBr(m-xylene)(PP)]Br, [RuI(m-xylene)(PP)]I, [RuCl(p-xylene) (PP)]Cl, [RuBr(p-xylene)(PP)]Br or [RuI(p-xylene)(PP)]I. Here, PP represents an optically active bisphosphine. Specific examples of the ruthenium compound (1) include [RuCl(p-cymene)((R)-binap)]Cl, [RuBr(p-cymene)((R)-binap)]Br, [RuI(p-cymene)((R)-binap)]I, [RuCl(mesitylene)((R)-binap)]Cl, [RuBr(mesitylene)((R)-binap)]Br, [RuI(mesitylene)((R)-binap)]I, [RuCl(toluene)((R)-binap)]Cl, [RuBr (toluene)((R)-binap)]Br, [RuI(toluene)((R)-binap)]I, [RuCl (o-xylene)((R)-binap)]Cl, [RuBr(o-xylene)((R)-binap)]Br, [RuI(o-xylene)((R)-binap)]I, [RuCl(m-xylene)((R)-binap)] Cl, [RuBr(m-xylene)((R)-binap)]Br, [RuI(m-xylene)((R)-binap)]I, [RuCl(p-xylene)((R)-binap)]Cl, [RuBr(p-xylene) ((R)-binap)]Br, [RuI(p-xylene)((R)-binap)]I, [RuCl(p-cymene)((R)-tol-binap)]Cl, [RuCl(benzene)((R)-tol-binap)] Cl, [RuCl(mesitylene)((R)-tol-binap)]Cl, [RuCl(toluene)

((R)-tol-binap)]Cl, [RuCl(o-xylene)((R)-tol-binap)]Cl, [RuCl(m-xylene)((R)-tol-binap)]Cl, [RuCl(p-xylene)((R)-tol-binap)]Cl, [RuCl(p-cymene)((R)-H$_8$-binap)]Cl, [RuCl(benzene)((R)-H$_8$-binap)]Cl, [RuCl(mesitylene)((R)-H$_8$-binap)]Cl, [RuCl(toluene)((R)-H$_8$-binap)]Cl, [RuCl(o-xylene)((R)-H$_8$-binap)]Cl, [RuCl(m-xylene)((R)-H$_8$-binap)]Cl, [RuCl(p-xylene)((R)-H$_8$-binap)]Cl, [RuCl(p-cymene)((R)-dm-binap)]Cl, [RuCl(benzene)((R)-dm-binap)]Cl, [RuCl(mesitylene)((R)-dm-binap)]Cl, [RuCl(toluene)((R)-dm-binap)]Cl, [RuCl(o-xylene)((R)-dm-binap)]Cl, [RuCl(m-xylene)((R)-dm-binap)]Cl, [RuCl(p-xylene)((R)-dm-binap)]Cl, [RuCl(p-cymene)((R)-segphos)]Cl, [RuCl(benzene)((R)-segphos)]Cl, [RuCl(mesitylene)((R)-segphos)]Cl, [RuCl(toluene)((R)-segphos)]Cl, [RuCl(o-xylene)((R)-segphos)]Cl, [RuCl(m-xylene)((R)-segphos)]Cl, [RuCl(p-xylene)((R)-segphos)]Cl, [RuCl(p-cymene)((R)-dm-segphos)]Cl, [RuCl(benzene)((R)-dm-segphos)]Cl, [RuCl(mesitylene)((R)-dm-segphos)]Cl, [RuCl(toluene)((R)-dm-segphos)]Cl, [RuCl(o-xylene)((R)-dm-segphos)]Cl, [RuCl(m-xylene)((R)-dm-segphos)]Cl, [RuCl(p-xylene)((R)-dm-segphos)]Cl, [RuCl(p-cymene)((R)-dtbm-segphos)]Cl, [RuCl(benzene)((R)-dtbm-segphos)]Cl, [RuCl(mesitylene)((R)-dtbm-segphos)]Cl, [RuCl(toluene)((R)-dtbm-segphos)]Cl, [RuCl(o-xylene)((R)-dtbm-segphos)]Cl, [RuCl(m-xylene)((R)-dtbm-segphos)]Cl and [RuCl(p-xylene)((R)-dtbm-segphos)]Cl. Among them, the following compounds are preferable: [RuCl(p-cymene)((R)-binap)]Cl, [RuCl(p-cymene)((R)-tol-binap)]Cl, [RuCl(p-cymene) ((R)-H$_8$-binap)]Cl, [RuCl(p-cymene) ((R)-dm-binap)]Cl, [RuCl(p-cymene) ((R)-segphos)]Cl, [RuCl(p-cymene) ((R)-dm-segphos)]Cl and [RuCl(p-cymene) ((R)-dtbm-segphos)]Cl. Note that, in these examples, only the optically active bisphosphines having an absolute configuration of (R) are exemplified. However, a ruthenium compound (1) with an optically active bisphosphine having an absolute configuration of (S) can be used, similarly.

In the formula (2), M represents a monovalent cation. Examples of the monovalent cation include alkali metals and ammonium (NH$_4$). The alkali metal is preferably sodium, potassium, lithium, or the like, and more preferably sodium.

In the formula (2), R$^1$ represents a group selected from the group consisting of alkyl groups, haloalkyl groups, phenyl groups optionally having a substituent, 1-aminoalkyl groups and 1-amino-1-phenylalkyl groups.

In the formula (2), an example of the alkyl group represented by R$^1$ is a linear or branched alkyl group having 1 to 10 carbon atoms, and preferably 1 to 6 carbon atoms. Specific examples of the alkyl group represented by R$^1$ include a methyl group, an ethyl group, a n-propyl group, an isopropyl group, a n-butyl group, an isobutyl group, a s-butyl group, a t-butyl group, a pentyl group and a hexyl group.

In the formula (2), an example of the haloalkyl group represented by R$^1$ is a linear or branched haloalkyl group having 1 to 10 carbon atoms, and preferably 1 to 4 carbon atoms. Specific examples of the haloalkyl group represented by R$^1$ include mono- and poly-haloalkyl groups such as a fluoromethyl group, a chloromethyl group, a difluoromethyl group, a dichloromethyl group, a trifluoromethyl group, a trichloromethyl group and a pentafluoroethyl group.

In the formula (2), R$^1$ may represent the phenyl group optionally having a substituent. Examples of the substituent that the phenyl group may have include: a linear or branched alkyl group having 1 to 4 carbon atoms, such as a methyl group, an ethyl group, an isopropyl group and a t-butyl group; a linear or branched alkoxy group having 1 to 4 carbon atoms, such as a methoxy group, an ethoxy group, an isopropoxy group and a t-butoxy group; a haloalkyl group having 1 to 4 carbon atoms, such as a trifluoromethyl group; a halogen atom such as a chlorine atom and a fluorine atom; a nitro group; and the like.

In the formula (2), an example of the alkyl group in the 1-aminoalkyl group represented by R$^1$ is a linear or branched alkyl group having 1 to 10 carbon atoms, and preferably 1 to 4 carbon atoms. Specific examples of the 1-aminoalkyl group represented by R$^1$ include an aminomethyl group, a 1-aminoethyl group, a 1-aminopropyl group and a 1-aminobutyl group.

In the formula (2), an example of the alkyl group in the 1-amino-1-phenylalkyl group represented by R$^1$ is a linear or branched alkyl group having 1 to 10 carbon atoms, and preferably 1 to 4 carbon atoms. Specific examples of the 1-amino-1-phenylalkyl group represented by R$^1$ include an aminophenylmethyl group, a 1-amino-1-phenylethyl group, a 1-amino-1-phenylpropyl group and a 1-amino-1-phenylbutyl group.

Specific examples of the carboxylate salt (2) used in the production method of the present invention include sodium acetate, ammonium acetate, potassium acetate, lithium acetate, sodium butyrate, sodium propionate, ammonium propionate, sodium isobutyrate, sodium valerate, sodium monochloroacetate, sodium monoiodoacetate, sodium dichloropropionate, sodium trichloroacetate, sodium trifluoroacetate, sodium trimethylacetate, sodium benzoate, ammonium benzoate, sodium 4-methylbenzoate, sodium 4-methoxybenzoate, sodium 4-trifluoromethylbenzoate, sodium 2-chlorobenzoate, sodium 2,6-dichlorobenzoate, sodium 4-fluorobenzoate and sodium 4-nitrobenzoate.

The amount of the carboxylate salt (2) used in the production method is normally 2 mol or more, preferably 2 mol to 10 mol, and more preferably 2 mol to 3 mol, relative to 1 mol of the ruthenium atom in the ruthenium compound (1).

In the production method, in order to produce the carboxylate complex (general formula (3)), the ruthenium compound (1) and the carboxylate salt (2) can be reacted with each other in a solvent.

The solvent is not particularly limited, as long as the solvent does not inhibit the reaction. Examples thereof include: alcohols such as methanol, ethanol and isopropyl alcohol; cyclic ethers such as tetrahydrofuran and dioxane; aromatic hydrocarbons such as toluene and xylene; halogenated hydrocarbons such as methylene chloride and dichloroethane; coordinating solvents such as acetonitrile and benzonitrile; and the like.

These solvents may be used alone or as a mixture of two or more kinds thereof. The amount of the solvent used is not particularly limited, but is normally 1 to 100 parts by weight, and preferably 5 to 20 parts by weight, relative to the neutral ligands.

The production method is preferably conducted under an atmosphere of an inert gas such as nitrogen gas or argon gas.

The reaction temperature is normally 30° C. or higher, and preferably 40° C. to 80° C.

After the reaction is completed, by subjecting the reaction mixture to desirable separation operations such as filtration, concentration, extraction, washing, and drying, a targeted carboxylate complex (general formula (3)) can be obtained.

Another method for producing a ruthenium complex represented by a general formula (3):

$$Ru(OCOR^1)_2(PP) \tag{3}$$

of the present invention is characterized in which a ruthenium compound represented by a general formula (7):

$$[RuX_2(L)]_n \tag{7}$$

(hereinafter, may be referred as a ruthenium compound (7)) is reacted with an optically active bisphosphine and a carboxylate salt represented by a general formula (2):

$$R^1CO_2M \qquad (2).$$

X and L in the general formula (7) and the optically active bisphosphine (PP) are the same as those in the general formula (1) described above. The general formula (2) is also as described above.

In the production method, in order to produce the carboxylate complex (general formula (3)), the ruthenium compound (7), the optically active bisphosphine and the carboxylate salt (2) can be reacted with one another in a solvent. Note that the ruthenium compound (7) can be easily obtained, for example, by heating, with stirring, ruthenium chloride (hydrate), α-phellandrene, and 1,3- or 1,4-cyclohexadiene, or the like, in a solvent such as ethanol. Alternatively, as the ruthenium compound (7), a commercially-available ruthenium compound can be used. Furthermore, by reacting the ruthenium compound (7) with the optically active bisphosphine, a ruthenium compound (1) can be obtained.

The solvent is not particularly limited, as long as the solvent does not inhibit the reaction. Examples thereof include: alcohols such as methanol, ethanol and isopropyl alcohol; cyclic ethers such as tetrahydrofuran and dioxane; aromatic hydrocarbons such as toluene and xylene; halogenated hydrocarbons such as methylene chloride and dichloroethane; coordinating solvents such as acetonitrile and benzonitrile; and the like. A preferable solvent is a solvent other than an amide compound.

These solvents may be used alone or as a mixture of two or more kinds thereof. The amount of the solvent used is not particularly limited, but is normally 1 to 100 parts by weight, and preferably 5 to 20 parts by weight, relative to the neutral ligands.

The production method is preferably conducted under an atmosphere of an inert gas such as nitrogen gas or argon gas.

The reaction temperature is normally 30° C. or higher, and preferably 40° C. to 80° C.

After the reaction is completed, by subjecting the reaction mixture to desirable separation operations such as filtration, concentration, extraction, washing, and drying, a targeted carboxylate complex (general formula (3)) can be obtained.

EXAMPLES

The present invention will be described in detail below with reference to the following non-limiting Examples and Comparative examples. Hereinbelow, the present invention will be described in details below with reference to the following non-limiting Examples. Note that, in the following Examples, all the solvents used had been degassed. NMR spectra were measured with a Mercury plus 300-4N spectrometer manufactured by Varian Technologies Japan Ltd. (300 MHz, internal standard substances: tetramethylsilane for $^1$H, 85% phosphoric acid aqueous solution for $^{31}$P).

Example 1

Synthesis of Ru(OAc)$_2$((R)-tol-binap)

[RuCl(p-cymene)(R)-tol-binap]Cl (1 g, 1.1 mmol), NaOAc.3 H$_2$O (455 mg, 3.3 mmol), toluene (7 ml) and ethanol (2.7 ml) were put into a flask, and stirred at 46° C. for 2 hours. The reaction liquid was washed with water several times, and concentrated to obtain 0.8 g of the title compound.

$^1$H-NMR (CDCl$_3$, δ ppm): 1.78 (6H, s), 1.85 (6H, s), 2.39 (6H, s), 6.28-7.74 (28H, m)

Example 2

Synthesis of Ru(OAc)$_2$((R)-tol-binap)

[RuCl$_2$(p-cymene)]$_2$ (612 mg, 1 mmol) and (R)-tol-BINAP (1.4 g, 2 mmol) were put into a flask, and air inside the flask was replaced with nitrogen. Then, toluene (14 ml) and methanol (1.4 ml) were added thereto, and stirred at 50° C. for 1 hour. Thereafter, NaOAc.3H$_2$O (0.82 g, 6 mmol) was added thereto, and the mixture was further stirred at the same temperature for 2 hours. The reaction liquid was washed with water several times, and concentrated to obtain 1.8 g of the title compound.

Example 3

Synthesis of Ru(OAc)$_2$((S)-binap)

[RuCl(p-cymene)(S)-binap] (1 g, 1.1 mmol), NaOAc.3H$_2$O (455 mg, 3.3 mmol), toluene (7 ml) and methanol (3 ml) were put into a flask, and stirred at 50° C. for 2 hours. The reaction liquid was washed with water several times, and concentrated to obtain 0.87 g of the title compound.

$^1$H-NMR (CDCl$_3$, δ ppm): 1.81 (6H, s), 6.5-7.86 (32H, m)

Example 4

Synthesis of Ru(OAc)$_2$((S)-binap)

[RuCl$_2$(p-cymene)]$_2$ (12.3 g, 80 mmol), (S)-BINAP (25 g, 40 mmol), toluene (240 ml) and ethanol (50 ml) were put into a flask, and stirred at 45° C. for 1 hour. Then, NaOAc.3H$_2$O (16 g, 12 mmol) was added thereto, and the mixture was stirred at the same temperature for 3 hours. The reaction liquid was washed with water several times. After the solvent was concentrated, heptane was added for crystallization to obtain 28.1 g of the title compound.

Example 5

Synthesis of Ru(OAc)$_2$((S)-binap)

[RuCl$_2$(benzene)]$_2$ (500 mg, 4 mmol), (S)-BINAP (1.2 g, 2 mmol), toluene (12 ml) and methanol (3 ml) were put into a flask, and stirred at 50° C. for 1 hour. Then, NaOAc.3H$_2$O (790 mg, 6 mmol) was added thereto, and the mixture was stirred at the same temperature for 2 hours. The reaction liquid was washed with water several times. After the solvent was concentrated, heptane was added to the resultant residue for crystallization to obtain 1.6 g of the title compound.

Example 6

Synthesis of Ru(OCOCH$_2$CH$_3$)$_2$((S)-binap)

[RuCl$_2$(p-cymene)]$_2$ (612 mg, 1 mmol) and (S)-BINAP (1.2 g, 2 mmol) were put into a flask, and air inside the flask was replaced with nitrogen. Then, toluene (12 ml) and methanol (3 ml) were added thereto, and the mixture was stirred at 50° C. for 1 hour. Thereafter, CH$_3$CH$_2$CO$_2$Na (576 mg, 6 mmol) was added thereto, and the mixture was further stirred at the same temperature for 2 hours. The reaction liquid was washed with water several times, and concentrated to obtain 1.7 g of the title compound.

$^1$H-NMR (CDCl3, δ ppm): 0.77 (6H, t, J=7.8 Hz), 1.97 (4H, q, J=7.5 Hz)), 6.42-7.72 (32H, m)

Example 7

Synthesis of Ru(OAc)$_2$((S)-segphos)

[RuCl$_2$(p-cymene)]$_2$ (612 mg, 1 mmol), (S)-SEGPHOS (1.22 g, 2 mmol), toluene (12 ml) and methanol (3 ml) were put into a flask, and stirred at 50° C. for 1 hour. Then, NaOAc.3H$_2$O (816 mg, 6 mmol) was added thereinto, and the mixture was stirred at the same temperature for 2 hours. The reaction liquid was washed with water several times, and concentrated to obtain 1.46 g of the title compound.

$^1$H-NMR (CDCl3, δ ppm): 1.76 (6H, s), 5.37 (2H, d, J=1.5 Hz), 5.72 (2H, d, J=1.2 Hz), 6.25 (2H, d, J=8.1 Hz), 6.47-6.53 (2H, m), 7.02-7.67 (20H, m)

Example 8

Synthesis of Ru(OAc)$_2$((S)-dm-segphos)

[RuCl$_2$(p-cymene)]$_2$ (12 g, 78 mmol), (S)-DM-SEGPHOS (28.3 g, 40 mmol), toluene (120 ml) and ethanol (24 ml) were put into a flask, and stirred at 45° C. for 1 hour. Then, NaOAc.3H$_2$O (10.7 g, 12 mmol) was added thereinto, and the mixture was stirred at the same temperature for 3 hours. The reaction liquid was washed with water several times. After the solvent was concentrated, heptane was added to the resultant residue for crystallization to obtain 33.2 g of the title compound.

$^1$H-NMR (CDCl$_3$, δ ppm): 1.68 (6H, s), 2.07 (12H, s), 2.33 (12H, s), 5.31 (2H, d, J=1.2 Hz), 5.70 (2H, d, J=1.2 Hz), 6.29-7.25 (16H, m)

Example 9

Synthesis of Ru(OAc)$_2$((S)-dtbm-segphos)

[RuCl$_2$(p-cymene)]$_2$ (306.2 mg, 1 mmol), (S)-DTBM-SEGPHOS (1.2 g, 1 mmol), THF (12 ml) and NaOAc (166 mg, 2 mmol) were put into a flask, and stirred at 64° C. for 3 hours. After the reaction was completed, the THF was concentrated. Then, 10 ml of toluene was added to the resultant residue, and then the resulting liquid was then washed with water several times and concentrated to obtain 1.2 g of the title compound.

$^{31}$P-NMR (CDCl$_3$, δ ppm) 66.63 (s)

Example 10

Synthesis of Ru(OAc)$_2$((S)-binap)

[RuCl$_2$(p-cymene)]$_2$ (1.2 g, 2 mmol), (S)-BINAP (2.5 g, 4 mmol) and NaOAc.3H$_2$O (1.6 g, 12 mmol) were put into a flask, and air inside the flask was replaced with nitrogen. Then, toluene (12 ml) and ethanol (2 ml) were added thereinto, and the mixture was stirred at 75° C. for 3 hours. The reaction liquid was washed with water several times, and concentrated to obtain 2.5 g of the title compound.

The invention claimed is:

1. A method for producing a ruthenium complex comprising the step of reacting a ruthenium compound represented by general formula (1):

[RuX(L)(PP)]X     (1), wherein
Ru represents a ruthenium atom,
X represents a halogen atom,
L represents an arene, and
PP represents an optically active bisphosphine,
with a carboxylate salt represented by general formula (2):

R$^1$CO$_2$M     (2), wherein
M represents a monovalent cation, and
R$^1$ represents a group selected from the group consisting of alkyl groups, haloalkyl groups, phenyl groups optionally having a substituent(s), 1-aminoalkyl groups and 1-amino-1-phenylalkyl groups,
to produce a ruthenium complex represented by general formula (3):

Ru(OCOR$^1$)$_2$(PP)     (3), wherein
R$^1$ represents a group selected from the group consisting of alkyl groups, haloalkyl groups, phenyl groups optionally having a substituent(s), 1-aminoalkyl groups and 1-amino-1-phenylalkyl groups, and
PP represents an optically active bisphosphine.

2. The production method according to claim 1, wherein the optically active bisphosphine in the general formula (1) is an optically active bisphosphine represented by the following formula (4) or (5):

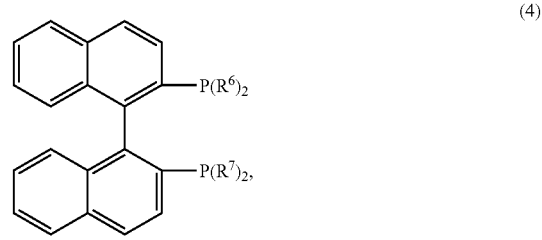

(4)

wherein
R$^6$ and R$^7$ each independently represent a phenyl group optionally having a substituent selected from the group consisting of halogen atoms, alkyl groups and alkoxy groups, a cyclopentyl group, or a cyclohexyl group, or

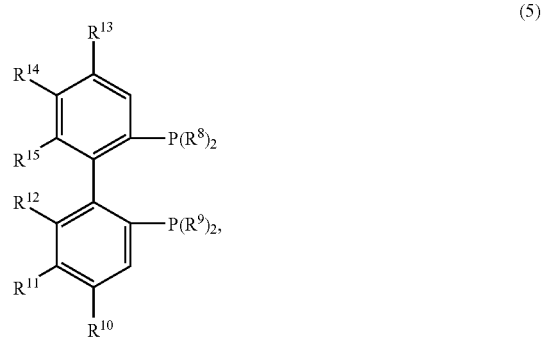

(5)

wherein
R$^8$ and R$^9$ each independently represent a phenyl group optionally having a substituent selected from the group consisting of halogen atoms, alkyl groups and alkoxy groups, a cyclopentyl group, or a cyclohexyl group,
R$^{10}$, R$^{11}$, R$^{13}$ and R$^{14}$ each independently represent an atom or a group selected from the group consisting of a hydrogen atom, alkyl groups, alkoxy groups, acyloxy groups, halogen atoms, haloalkyl groups and dialkylamino groups, R$^{12}$ and R$^{15}$ each independently represent a group selected from the group consisting of alkyl groups, alkoxy groups, acyloxy groups, halogen atoms, haloalkyl groups and dialkylamino groups, any two groups of R$^{10}$, R$^{11}$ and R$^{12}$ optionally together form a methylene chain optionally having a substituent, or a (poly)methylenedioxy group optionally having a substituent, any two groups of R$^{13}$, R$^{14}$ and R$^{15}$ optionally together form a methylene chain optionally having a substituent, or a (poly)methylenedioxy group optionally having a substituent, and R$^{12}$ and R$^{15}$ optionally together form a methylene chain optionally having a substituent, or a (poly)methylenedioxy group optionally having a substituent.

3. A method for producing a ruthenium complex comprising the step of reacting a ruthenium compound represented by general formula (7):

[RuX$_2$(L)]$_n$     (7), wherein

Ru represents a ruthenium atom,

X represents a halogen atom,

L represents an arene, and n represents a natural number of 2 or higher, with an optically active bisphosphine and a carboxylate salt represented by general formula (2):

R$^1$CO$_2$M     (2), wherein

M represents a monovalent cation, and

R$^1$ represents a group selected from the group consisting of alkyl groups, halogenated alkyl groups, phenyl groups optionally having a substituent(s), 1-aminoalkyl groups and 1-amino-1-phenylalkyl groups, to produce a ruthenium complex represented by general formula (3):

Ru(OCOR$^1$)$_2$(PP)     (3), wherein

R$^1$ represents the group selected from the group consisting of alkyl groups, halogenated alkyl groups, phenyl groups optionally having a substituent(s), 1-aminoalkyl groups and 1-amino-1-phenylalkyl groups, and PP represents the optically active bisphosphine, wherein the method uses a solvent other than an amid compound.

4. The production method according to claim 3, wherein the optically active bisphosphine is an optically active bisphosphine represented by the following formula (4) or (5):

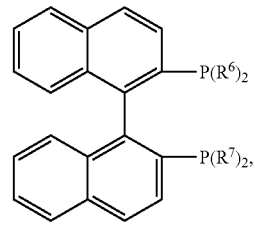

(4)

wherein
R$^6$ and R$^7$ each independently represent a phenyl group optionally having a substituent selected from the group consisting of halogen atoms, alkyl groups and alkoxy groups, a cyclopentyl group, or a cyclohexyl group, or

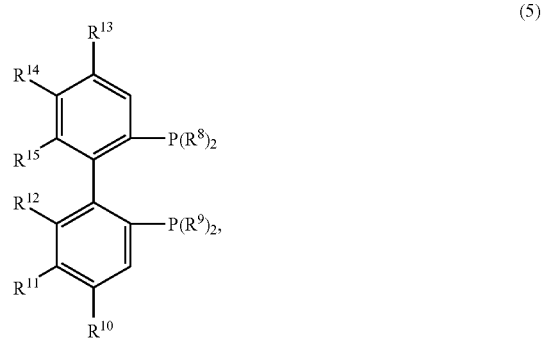

(5)

wherein
R$^8$ and R$^9$ each independently represent a phenyl group optionally having a substituent selected from the group consisting of halogen atoms, alkyl groups and alkoxy groups, a cyclopentyl group, or a cyclohexyl group, R$^{10}$, R$^{11}$, R$^{13}$ and R$^{14}$ each independently represent an atom or a group selected from the group consisting of a hydrogen atom, alkyl groups, alkoxy groups, acyloxy groups, halogen atoms, haloalkyl groups and dialkylamino groups, R$^{12}$ and R$^{15}$ each independently represent a group selected from the group consisting of alkyl groups, alkoxy groups, acyloxy groups, halogen atoms, haloalkyl groups and dialkylamino groups, any two groups of R$^{10}$, R$^{11}$ and R$^{12}$ optionally together form a methylene chain optionally having a substituent, or a (poly)methylenedioxy group optionally having a substituent, any two groups of R$^{13}$, R$^{14}$ and R$^{15}$ optionally together form a methylene chain optionally having a substituent, or a (poly)methylenedioxy group optionally having a substituent, and R$^{12}$ and R$^{15}$ optionally together form a methylene chain optionally having a substituent, or a (poly)methylenedioxy group optionally having a substituent.

* * * * *